United States Patent
Kim

(10) Patent No.: US 6,786,365 B2
(45) Date of Patent: Sep. 7, 2004

(54) LIQUID SUPPLY APPARATUS

(75) Inventor: Yong-Nyun Kim, 215-1004 Hangaram Apartment, 407 Ichon- 1-Dong, Yongsan-Gu, Seoul 140-728 (KR)

(73) Assignee: Yong-Nyun Kim, Seoul (KR)

( * ) Notice: Subject to any disclaimer, the term of this patent is extended or adjusted under 35 U.S.C. 154(b) by 0 days.

(21) Appl. No.: 10/350,165

(22) Filed: Jan. 21, 2003

(65) Prior Publication Data

US 2003/0168480 A1 Sep. 11, 2003

Related U.S. Application Data

(63) Continuation of application No. PCT/KR00/01530, filed on Dec. 23, 2000.

(30) Foreign Application Priority Data

Jul. 22, 2000 (KR) .......................................... 2000-42128
Oct. 28, 2000 (KR) .......................................... 2000-63790

(51) Int. Cl.$^7$ ............................................. B67D 5/42
(52) U.S. Cl. ..................................... 222/389; 222/394
(58) Field of Search .............................. 222/389, 394, 222/333, 390, 39

(56) References Cited

U.S. PATENT DOCUMENTS

| | | | |
|---|---|---|---|
| 4,445,896 A | | 5/1984 | Gianturco |
| 4,596,557 A | | 6/1986 | Pexa |
| 4,597,758 A | | 7/1986 | Aalto et al. |
| 4,624,664 A | | 11/1986 | Peluso et al. |
| 4,744,442 A | * | 5/1988 | Bras et al. ..................... 184/39 |
| 4,813,937 A | * | 3/1989 | Vaillancourt ................ 604/131 |
| 5,312,389 A | * | 5/1994 | Theeuwes et al. ....... 604/892.1 |
| 5,522,526 A | * | 6/1996 | DeLaforcade et al. ......... 222/1 |
| 5,992,700 A | | 11/1999 | McGlothlin et al. |

FOREIGN PATENT DOCUMENTS

| | | |
|---|---|---|
| EP | 0 406 584 A1 | 1/1990 |
| JP | 2102664 | 4/1990 |
| JP | 02-102664 | 4/1990 |
| JP | 4312469 | 11/1992 |
| JP | 04-312469 | 11/1992 |
| KR | 98-24858 | 7/1998 |
| KR | 20-150725 | 4/1999 |
| KR | 20-0150725 | 4/1999 |
| KR | 1002629300000 | 5/2000 |
| KR | 20-205619 | 7/2000 |

* cited by examiner

Primary Examiner—Philippe Derakshani

(57) ABSTRACT

A liquid supply apparatus (10) is provided. The liquid supply apparatus (10) has a cylinder (12), a piston (14) and a piston pushing apparatus. The cylinder (12) is provided with a head portion (20) with outlet (24). The cylinder (12) has a rear end opened. The piston (14) is inserted into the cylinder (12). The piston moves along the longitudinal direction of the cylinder (12) so as to inject liquid contained in the cylinder (12). The piston pushing apparatus (16) pushes the piston (14). The piston pushing apparatus (16) has a moving member contacting the rear portion of the piston (14), a electric motor and a movement transferring mechanism. The movement transferring mechanism converts the rotation of the motor into the linear movement of the moving member.

29 Claims, 12 Drawing Sheets

US 6,786,365 B2

LIQUID SUPPLY APPARATUS

RELATED APPLICATIONS

This application claims for the benefit of an earlier filing date under 35 U.S.C. § 365 (c) of International Application No. PCT/KR00/01530 filed Dec. 23, 2000, designating the United States and claiming for the benefit of the earlier filing dates under 35 U.S.C. § 365 (b) of Korean Patent Application Nos. 2000/42128 filed Jul. 22, 2000, and 2000/63790 filed Oct. 28, 2000, which are hereby incorporated herein by reference in their entirety. International Application No. PCT/KR00/01530 was published in English as WO 02/11791 A1 on Feb. 14, 2002, and is hereby incorporated herein by reference in its entirety.

BACKGROUND OF THE INVENTION

1. Field of the Invention

The present invention relates to a liquid supply apparatus, more particularly to a portable liquid supply apparatus that is constructed so that liquid medicine, etc. is supplied in a constant quantity per unit time.

2. Description of the Related Art

There are a number of cases where certain kinds of medicine should be injected into a patient in a constant quantity per unit time and over a long period of time. The example of the medicine is an anodyne that is dosed to a patient feeling serious pain. Unless the anodyne is dosed to a patient in a constant quantity per unit time, the patient may feel pain.

An apparatus for injecting such a medicine by pushing, in a constant speed, a plunger of a common syringe mounted to the apparatus, is known. It is unsuitable for a patient to carry the conventional apparatus due to its large size.

A kind of a medicine injection apparatus capable of being carried by a patient is currently being used. The portable medicine injection apparatus is a structure in which a resilient bladder made of rubber material is provided in a cylindrical chamber. An inlet and an outlet are formed on the resilient bladder. The bladder inflates as the medicine is injected thereinto through the inlet. A small tube is attached to the outlet through which the medicine gradually draws off. The medicine (an injection) is discharged in a small amount and injected in droplet form at a site, such as a vein or an epidural space of a patient, where a medical doctor targets.

In a medicine injection apparatus using its resiliency, the resilient bladder may cause some problems. Inferior goods, in which thickness of the bladder is not uniform and fine holes are formed thereon, may be manufactured. The inferiority affects the resiliency of the bladder which, in turn, cannot have the desired resiliency. If this is the case, it is impossible to dose the medicine to the patient in a constant quantity per unit time. Furthermore, a medical doctor cannot beforehand treat the inferiority since it is usually discovered during the use of the bladder.

A medicine injection apparatus using a bladder and an elastic body is proposed. The resilient bladder or elastic body has such a problem that its resiliency or elasticity may be varied in accordance with the quantity of the medicine contained therein. There is also the following shortcoming. That is, the medicine is injected into the bladder or body in an excessively larger quantity than the doctor targets since an external force (elasticity of the elastic body) affecting on a liquid flow is too large at an early period of the injection, whereas the medicine is injected in an amount much smaller than the target at a late period of the injection since the external force is too small.

SUMMARY OF THE INVENTION

Therefore, various functions are required when the liquid supply apparatus is especially used for the medicine injection apparatus. First of all, the function of maintaining a constant medicine injection quantity per unit time is required. It is preferred that variation of the medicine injection quantity per unit time be minimized. Portability makes the apparatus convenient. Further, it is preferred that the medicine injection apparatus be constructed to have low possibility of inferiority occurrence in the parts.

It is preferred that the medicine injection apparatus be capable of setting an injection quantity per unit time (hereinafter, referred to as "injection speed"). It is more preferred that the apparatus be constructed to permit possibility of arbitrary changes of the setting by a user (a patient) to be limited after once setting the injection quantity per unit time. The reason is that in general, the medicine such as an anodyne should be injected in a constant quantity, and the injection quantity of the medicine should be predetermined and injected under supervision of the doctor. Further, the patient should not be able to adjust the injection quantity of the medicine. Therefore, a locking function is required for preventing the patient from changing the injection quantity per unit time, at least after it is set, pursuant to the doctor's instructions and under his supervision. Nevertheless, the patient can increase the injection quantity per unit time to an extent within a specific range that had been set by the doctor. The reason is why the medicine injection quantity can be increased within a limited range if the patient's pain is getting serious.

It is also preferred that the medicine injection apparatus be constructed to interrupt the medicine injection by automatically detecting whether the medicine is not further injected. The reason is that it is required to cope with the problems when an injection syringe gets removed, when the patient is subjected to an intravenous injection.

In addition to these characteristics, it is still preferred that the medicine injection apparatus be constructed so as to minimize the possibility of introduction of air into the patient's body together with the medicine when the medicine is injected to the patient. Minimization of leakage during the injection should also be considered.

An aspect of the present invention provides a liquid supply apparatus. The liquid supply apparatus comprises: a cylinder having an interior space, a head portion and a rear portion, the head portion having a liquid-flow opening; a piston located in the interior space of the cylinder and air-tightly partitioning the interior space into a liquid compartment on the side of head portion and a gas compartment on the side of the rear portion; a gas supply apparatus configured to be coupled to the rear portion and to supply a gas into the gas compartment; and wherein the piston is configured to move toward the head portion when the gas is supplied to the gas compartment.

In the liquid supply apparatus, the gas supply apparatus comprises a solid material and a liquid material capable of generating the gas by a chemical reaction thereof. The solid material contains a metal carbonate. The solid material comprises 70–95 wt % of sodium bicarbonate ($NaHCO_3$), 3–30 wt % of gelatin, and no more than 3 wt % of talc. The solid material comprises 90–94 wt % of sodium bicarbonate ($NaHCO_3$), 5–10 wt % of gelatin, and no more than 1 wt % of talc. The liquid material is a solution of L-tartaric acid ($C_4H_6O_6$). The gas supply apparatus is configured to generate the gas at a pressure from about 0.35 kg/cm² to about 0.50 kg/cm².

In the liquid supply apparatus, the gas supply apparatus comprises: a first material; a second material; a breakable partition isolating the first and second materials from each other; a reaction vessel where the first and second materials react with each other when the partition is broken; and a partition breaker configured to break the breakable partition so as to let the first and second material contact each other in the reaction vessel. Either of the first and second materials is a liquid, and the reaction vessel is a container containing the liquid. The gas supply apparatus further comprises a gas collecting structure comprising a liquid-impermeable-but-gas-permeable sheet arranged to contact the liquid. The liquid-impermeable-but-gas-permeable sheet is placed on a wall of the reaction vessel such that at least a portion of the sheet is exposed to the gas generated from the reaction. The gas collecting structure further comprises a gas-passage sheet and a liquid-and-gas-impermeable sheet, and wherein the gas-passage sheet is located between the liquid-impermeable-but-gas-permeable sheet and the liquid-and-gas-impermeable sheet. The gas-passage sheet is made of non-woven fabric or foam material. The gas supply apparatus further comprises a gas pressure regulator configured to control or regulate the pressure of the gas supplied into the gas compartment.

Still in the liquid supply apparatus, the head portion of the cylinder comprises a projection extending into the interior space and has a longitudinal through-hole, the through-hole constituting the liquid-flow opening. The piston has a leading end facing the projection, wherein the piston has a recess on the leading end thereof, and wherein the recess is configured to receive the projection. The recess is further configured to substantially contact with the projection when receiving the projection. The liquid supply apparatus further comprises a tube connected to the cylinder via the through-hole of the projection, wherein the tube is in fluid communication with the liquid compartment. The liquid supply apparatus further comprises a cap configured to cover a distal end of the tube, the cap having a through-hole in fluid communication with the tube, the cap further comprising a gas-permeable-but-liquid-impermeable material located between the through-hole and the distal end of the tube. The piston has a recess on a trailing end thereof.

Another aspect of the present invention provides a method of continuously supplying a liquid for an extended period of time. The method comprises: providing the liquid supply apparatus of Claim 1; filling the liquid compartment with a liquid; activating the gas supply apparatus so as to supply the gas into the gas compartment, wherein the gas supply apparatus continuously supplies the gas into the gas compartment for an extended period of time; and wherein the piston is moved toward the head portion as a gaseous pressure within the gas compartment increases, whereby the liquid in the liquid compartment flows out of the liquid compartment through the liquid-flow opening. In the method, the liquid is a liquid medication.

Still another aspect of the present invention provides a liquid supply apparatus. The apparatus comprises: a cylinder having a head portion and an interior space, wherein the head portion of the cylinder has a projection extending into the interior space and a longitudinal through-hole in the projection; a piston located in the interior space of the cylinder and air-tightly partitioning the interior space into two compartments; and wherein the piston has a leading end facing the projection and a recess on the leading end thereof, the recess being configured to receive the projection. The recess is further configured to substantially contact with the projection when receiving the projection. The liquid supply apparatus further comprises a tube connected to the cylinder via the through-hole of the projection, wherein the tube is in fluid communication with the liquid compartment. The piston has a recess on a trailing end thereof. The piston comprises a cylindrical body and a sealing ring, wherein the cylindrical body has an annular groove on an outer surface thereof, and wherein the sealing ring is fitted around the groove.

A further aspect of the present invention provides a cap for covering a liquid supply tube. The cap comprises: a cap body configured to receive an end of a liquid supply tube; a through-hole formed on the cap body, the through-hole being in fluid communication with the liquid supply tube; a gas-permeable-but-liquid-impermeable material located between the through-hole and the distal end of the tube; and wherein the material allows passage of a gas from the tube through the through-hole while preventing passage of a liquid through the through-hole. The cap body is configured to tightly receive the end of the liquid supply tube.

According to an aspect of the present invention, the liquid supply apparatus that is capable of injecting the liquid in a constant injection speed over a long time period is provided.

According to an aspect of the present invention, there is provided a liquid supply apparatus comprising an elongated cylinder provided with an outlet at a front head portion thereof, a piston inserted into the cylinder for moving along the length of the cylinder and pushing out liquid within the cylinder through the outlet, and a piston pushing apparatus mounted on an opened rear portion of the cylinder for pushing the piston toward the head portion at a generally constant speed, wherein the piston pushing apparatus includes a moving member for contacting a rear portion of the piston and moving linearly within the cylinder, a driving motor, and a movement transferring mechanism for transferring the drive of the driving motor to the moving member.

According to another aspect of the present invention, there is provided a liquid supply apparatus comprising an elongated cylinder provided with an outlet at a front head portion thereof, and a piston inserted into the cylinder for moving along the length of the cylinder and pushing out liquid within the cylinder through the outlet, wherein the head portion of the cylinder is formed with a projection extending therefrom toward the interior of the cylinder, the outlet of the head portion is formed by providing the projection with a longitudinal through-hole, and a leading end of the piston is provided with a recess for receiving the projection.

According to a further aspect of the present invention, there is provided a liquid supply apparatus comprising an elongated cylinder provided with an outlet at a front head portion thereof, a piston inserted into the cylinder for moving along the length of the cylinder and pushing out liquid within the cylinder through the outlet, and a piston pushing apparatus mounted on an opened rear portion of the cylinder for pushing the piston toward the head portion, wherein the piston pushing apparatus includes a gas supply apparatus for supplying gas to a portion of the cylinder behind the piston so as to push the piston, wherein the gas supply apparatus comprises a first chamber for accommodating one of solid and liquid materials that can generate gas by a mutual chemical reaction, a second chamber for accommodating the other of the solid and liquid materials, a gas passage connected to the second chamber, and a liquid-impermeable but gas-permeable filter disposed in the second chamber or the gas passage. The second chamber is separated from the first chamber but is able to communicate with the first chamber by a user's operation.

BRIEF DESCRIPTION OF THE DRAWINGS

These and other objects and features of the present invention will be apparent to those skilled in the art upon reading and understanding the following detailed description of the preferred embodiment of the invention with reference to the following drawings in which.

DETAILED DESCRIPTION OF THE PREFERRED EMBODIMENTS

Figure 1:
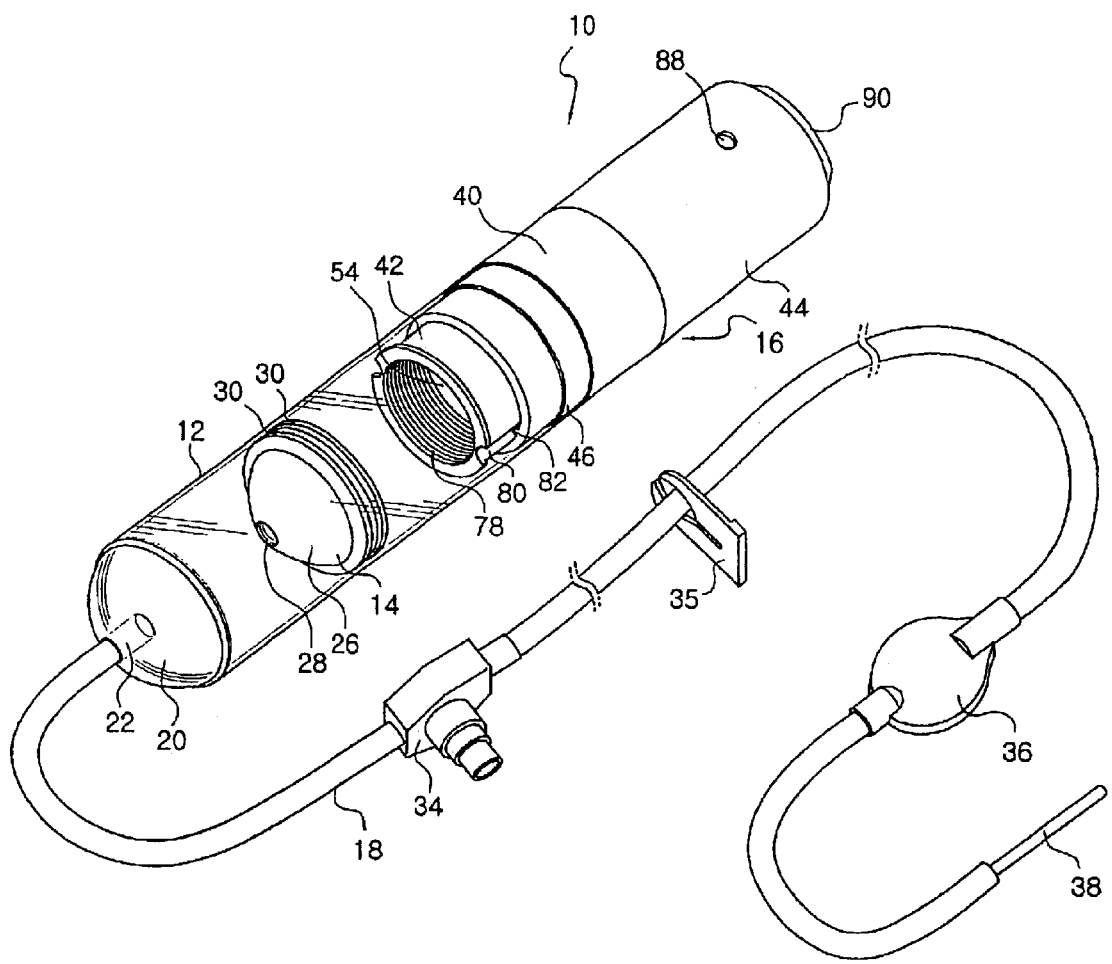
FIG. 1 is a perspective view of a medicine injection apparatus according to an embodiment of the present invention.
Figure 1:
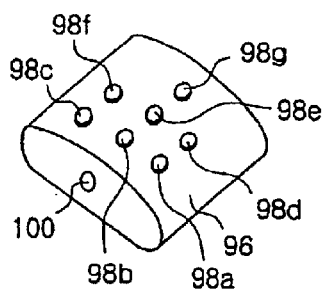

Hereinafter, preferred embodiments of the present invention will be explained in detail with reference to the drawings.

Referring to FIGS. 1 to 4, a medicine injection apparatus 10 comprises a cylinder 12, a piston 14 and a piston pushing apparatus 16. The piston 14 is fitted into the cylinder 12. A tube 18 is connected to a front end of the cylinder 12. The piston pushing apparatus 16 is intended to move the piston 14 toward a head portion 20 of the cylinder 12 generally at a constant speed.

Figure 2:
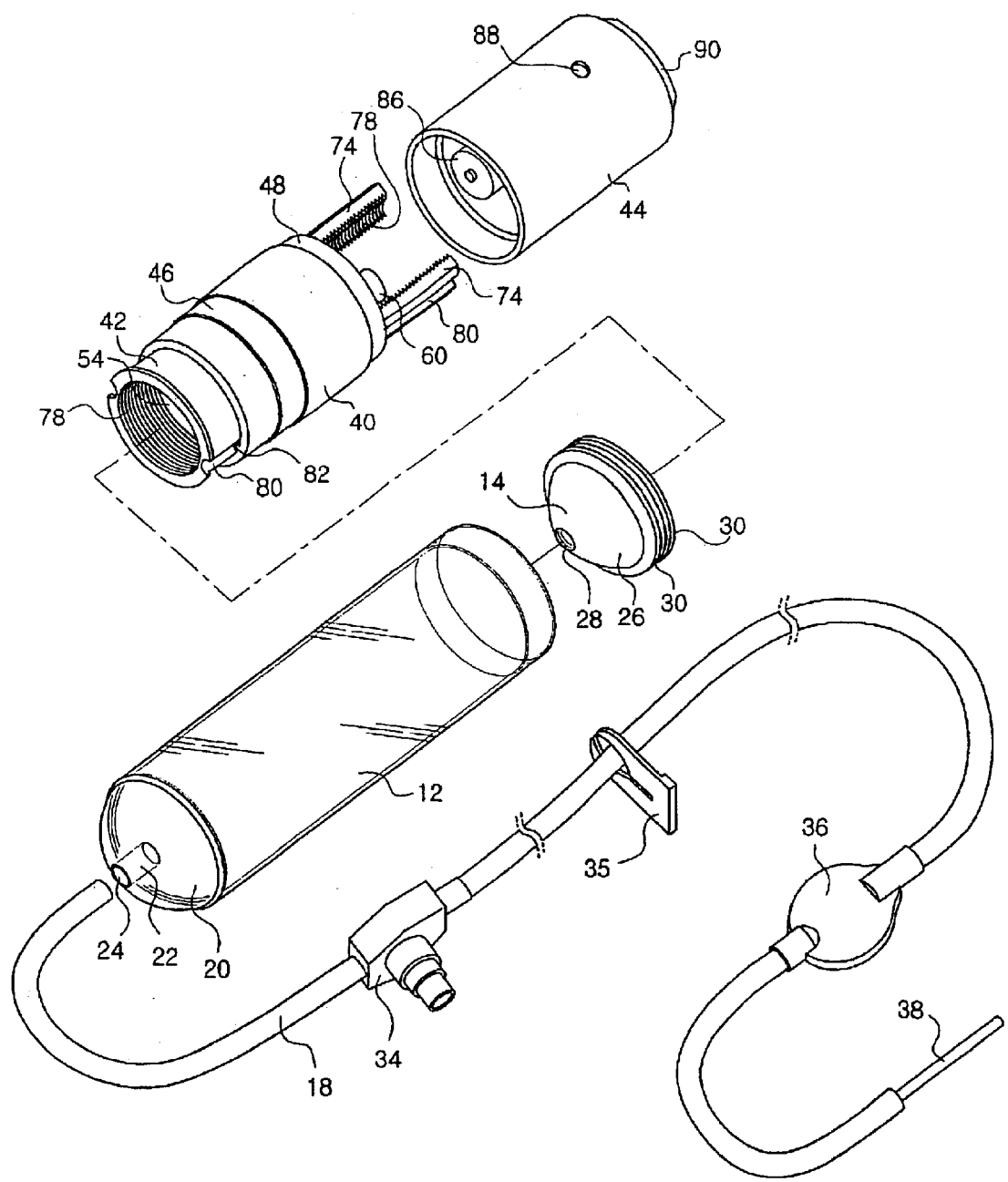
FIG. 2 is an exploded perspective view of the medicine injection apparatus shown in FIG. 1.
Figure 3:
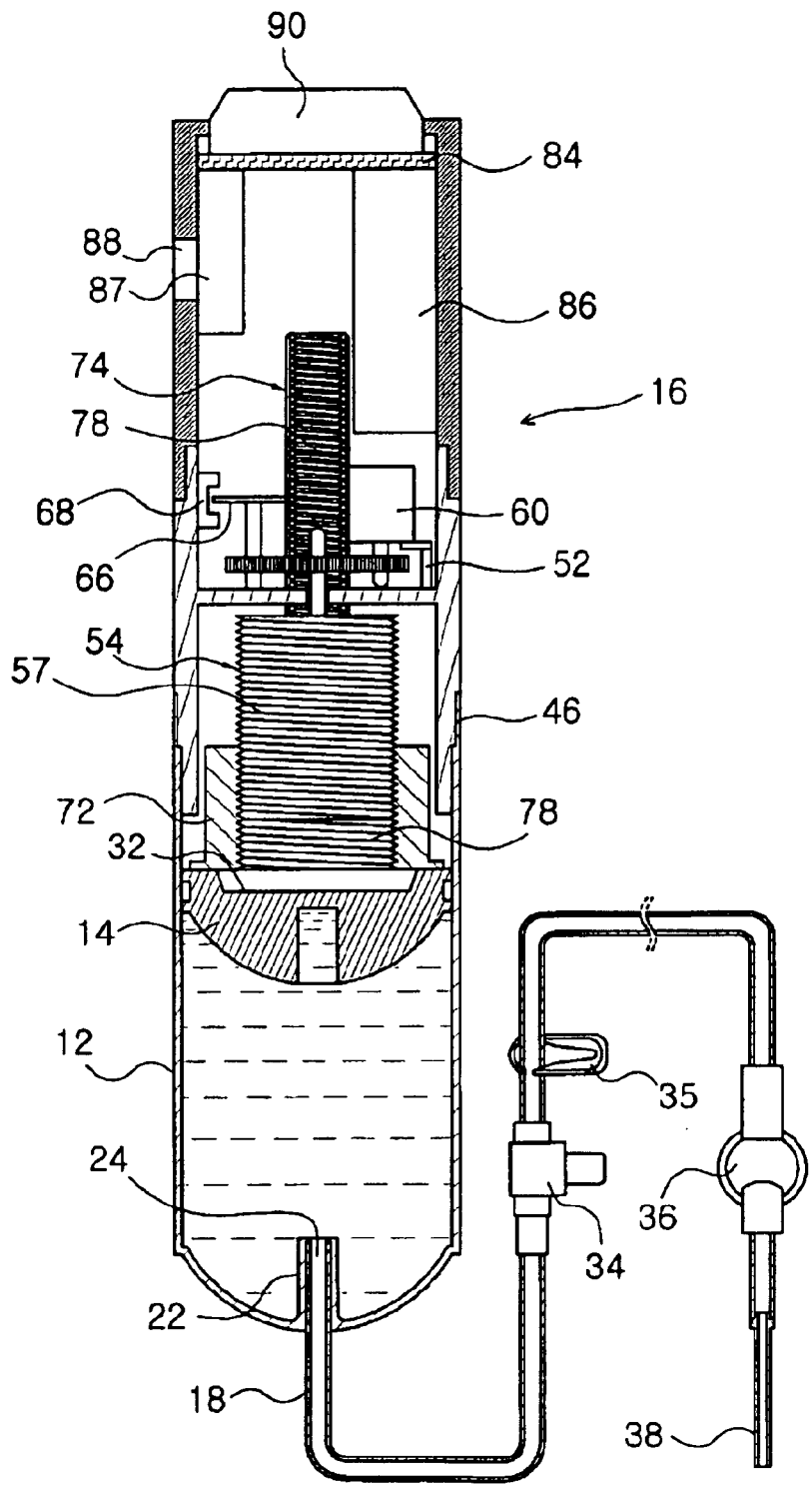
FIG. 3 is a sectional view of the medicine injection apparatus shown in FIG. 1.
Figure 4:
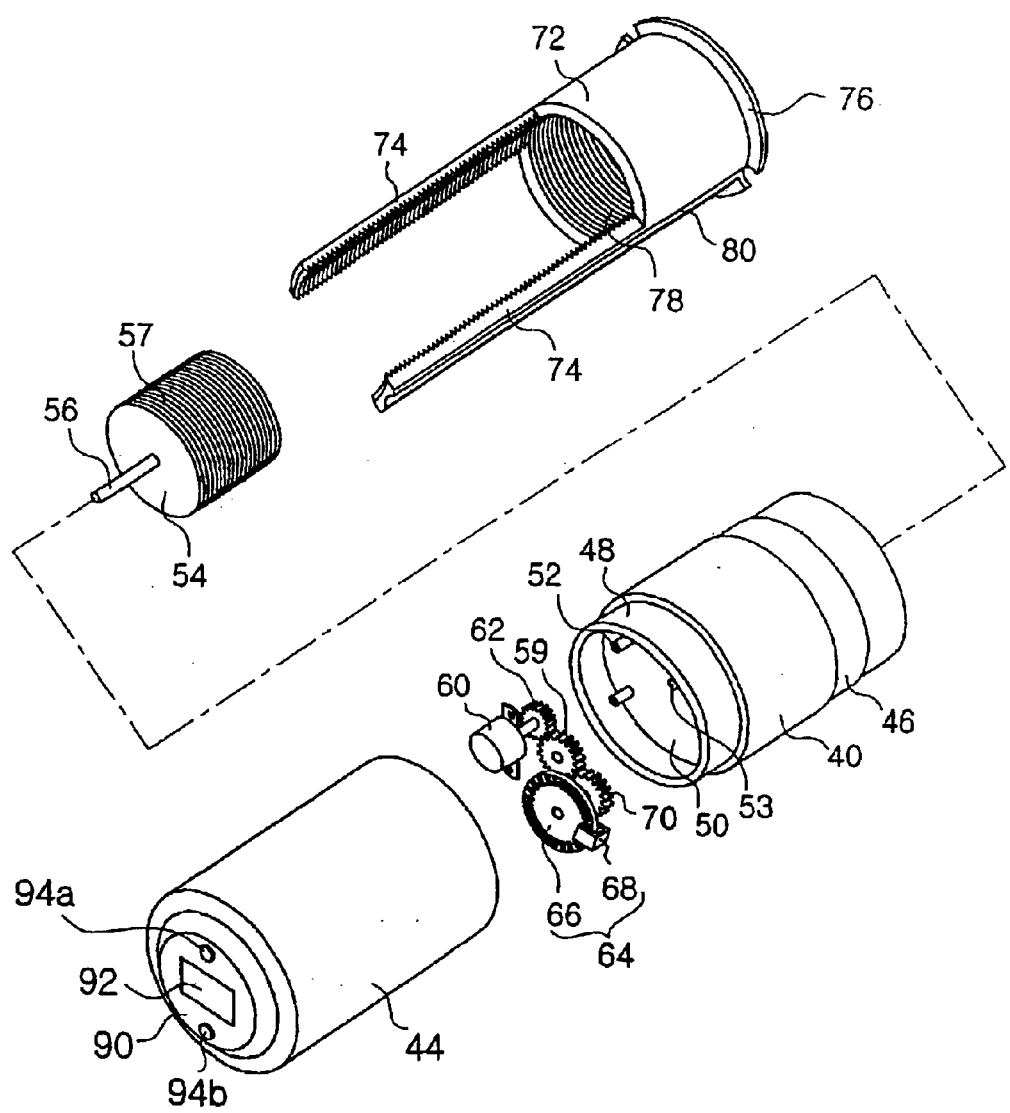
FIG. 4 is an exploded perspective view of a piston pushing apparatus of the medicine injection apparatus shown in FIG. 1.

The cylinder 12 is hollow and cylindrical, and is generally made of transparent plastic resin material. Although it is not shown, a scale is printed onto an external surface of the cylinder. Referring to FIGS. 1 to 3, the head portion 20 of the cylinder 20 has a generally hemispherical shape and protrudes outwards. (However, the present invention is not limited to the above.) An exhaust projection 22, protruding into the cylinder, is formed at a center of the head portion 20.

The exhaust projection 22 is formed with a through hole 24. An end of the tube 18 to be described hereinafter is inserted into and fixed to the hole 24. Since the exhaust projection 22 extends to protrude inwards, risk that it is damaged by external factors is remarkably reduced. The piston pushing apparatus 16 is installed onto a rear distal end of the cylinder 12, which is opened.

The piston 14 is generally made in the form of a disk having a thickness (or a cylinder having a low height) such that it is inserted into the cylinder 12. A leading end portion 26 of the piston 14 is formed to be hemispherical such that it conforms well to an inner side of the head portion 20. A hole 28 is provided at a center of the leading end portion 26. The exhaust projection 22 is fitted into the hole 28. The hole is sized such that a medicine can pass through a space formed between the projection and the hole when the projection is inserted into the hole.

An annular peripheral projection 30 is provided around the piston 14. A distal end portion of the annular peripheral projection 30 comes into contact with an inner surface of the cylinder 12 and prevents a medicine from escaping between them. Two annular peripheral projections 30 may be formed and arranged. The peripheral projections 30 prevent the medicine from escaping or a gas from being introduced into the medicine, and prevent the piston 14 from being slanted during operation. A circular recess 32, deeply hollowed, is formed at a rear portion of the piston 14. (See FIG. 3.)

The tube 18 is inserted into and fixed to the hole of the exhaust projection 22. With such a structure, possibility that the tube is bent will be reduced. In the tube 18 are installed various components required for the medicine injection, such as a supply valve member (T-shaped valve) 34 for the medicine injection, a clamp 35 for preventing the medicine from being injected when necessary, a filter 36 for filtering foreign material from the medicine and for removing a gas from the injection, etc. Another end 38 of the tube 18 is, for example, connected to a passage that is communicated with a catheter or an injection needle inserted into a vein of the patient.

Referring to FIGS. 1 to 4, the piston pushing apparatus 16 includes a supporting body 40, a moving member 42 and a housing 44. As shown specifically in FIG. 3, the piston pushing apparatus 16 includes a stepped portion 46, which has an outer diameter smaller than the inner diameter of the supporting body 40 and is located at the front of the supporting body, such that the stepped portion can be inserted into and fixed to a rear end of the cylinder 12. The stepped portion 46 is fitted into the cylinder 12. After the piston pushing apparatus 16 is inserted into the cylinder 12, they should be firmly fastened to each other by means of an adhesive tape, etc. Otherwise, they may be threaded together by respectively forming male thread and female thread on both sides thereof.

The supporting body 40 is generally cylindrical. The stepped portion 46 is provided at the front thereof as described above, and a stepped portion 48 onto which the housing 44 to be described hereinafter is fitted is provided at the rear. A supporting plate 50 is provided at the inner side thereof. Bosses 52 protrude afterward in the supporting plate 50. A motor that will be described hereinafter is fixed to the bosses 52. A through hole 53 is provided at the center of the supporting plate 50, and a bearing is installed in the hole although it is not described in detail.

A rotating screw block 54 is disposed in the front space of the supporting plate 50. A shaft 56 is provided at the center of the rotating screw block 54. The shaft 56 extends toward the rear space of the supporting body 40 through the hole 53 of the supporting plate 50. A gear 59 for forming a power transmission mechanism 58 is fitted into and fixed at the shaft 56. The rotating screw block 54 takes a cylindrical shape, and a screw 57 for power transmission (a lead screw) is formed at the peripheral face of the block. Although not described in detail, the rotating screw block 54 is supported in a manner that it cannot move in a longitudinal direction of the cylinder 12 but that it can rotate.

The motor 60 for causing the rotating screw block 54 to rotate is fixed to the bosses 52 of the supporting plate 50. It is preferred that the motor 60 be precisely controlled in view of its rotational speed. In this embodiment, the motor 60 comprises a stepping motor. The motor 60 is preferred to be a low-voltage and low-power motor. The rotational driving force of the motor 60 is transmitted to the rotating screw block 54 through a gear 62 and a gear 59. A lead wire, which is in turn connected to a circuit board to be described hereinafter, is attached to the motor 60, although it is not shown.

In addition, a sensor device 64 is disposed at the rear portion of the supporting body 40. The sensor device 64 comprises a rotary encoder 66 and a sensing portion 68. The sensing portion includes a light-emitting element and a light-receiving element that are disposed at both sides of the rotary encoder 66, respectively. In the meantime, a gear 70 is installed at a rotating central shaft of the rotary encoder 66. The gear 70 engages with the gear 59. Therefore, the rotation or stop of the rotating screw block 54 is transmitted to and detected by the rotary encoder 66. A lead wire (not shown) is connected to the sensing portion, and then the lead wire is connected to the circuit board to be described hereinafter.

The moving member 42 can be moved in a longitudinal direction so as to cause the piston 14 to be pushed. As well shown in FIG. 4, the moving member 42 includes a hollow cylindrical body 72 and rod portions 74. A flange 76 is formed at a leading end of the hollow cylindrical body 72. The flange 76 comes into contact with the rear face of the piston 14 to cause the piston 14 to be pushed. Contrary to the shown embodiment, the leading end of the hollow cylindrical body 72 may be constructed to come into contact with an inclined side wall of the circular recess provided in the rear portion of the piston 14. In this case, the leading end of the hollow cylindrical body pushes the side wall of the piston as well as a rearmost portion of the piston, and thus, the peripheral projections can come into more close contact with the inner wall of the cylinder.

The two rods 74, which are disposed opposite to each other, extend backwards from the hollow cylindrical body 72. Thread 78 is formed on the inner face of the hollow cylindrical body 72 and on the opposite faces of the rods. The thread 78 is used for power transmission and engages with the thread 57 that is formed on the external face of the rotating screw block 54. Therefore, as the rotating screw block 54 rotates, the two threads engage and rotate together, and then the moving member 42 moves in a longitudinal direction.

The moving member 42 is provided with guide grooves 80 that are formed on opposite external surfaces of both the hollow cylindrical body 72 and the rods 74. The guide grooves 80 cooperate with guide projections 82, formed on the internal surfaces of the supporting body, in order to cause the moving member 42 to move in a longitudinal motion. Further, the supporting plate of the supporting body 40 is provided with the holes through which the rods 74 can pass, although the holes are not specifically shown.

The housing 44 is fitted into and fixed to the rear portion of the supporting body 40. The circuit board 84 is fixed onto an inner side of the housing 44. Various circuit elements are installed on the circuit board 84. An electric cell (a battery) 86 is also fixed to the inner side of the housing 44. Lead wires of the cell 86, the motor 60 and the sensing device 64 are connected at proper positions on the circuit board 84, and they supply an electric power, and transmit/receive the driving signals or sensing signals.

As well, an infrared receiving device 87 is connected to and installed on the circuit board 84. The infrared receiving device is used for receiving the signals from a remote controller to be described hereinafter. To this end, the housing 44 is provided with a port hole 88.

A front panel 90 is provided in an external face of the housing 44. The front panel is provided with a liquid crystal display 92 and buttons 94a and 94b. The front panel is generally fixed to the circuit board 84. Characters or numerals for indicating an operating state or a setting state of the injection apparatus are displayed onto the liquid crystal display 92. The button 94a is a start/stop button for causing the operation of the injection apparatus to start or stop. The button 94b is a button for temporarily changing an injection quantity per unit time, which indicates an injection quantity of the medicine to be increased by a predetermined quantity and to be injected. The buttons 94a and 94b are provided in the piston pushing apparatus 16 so that the patient can actuate these buttons.

Referring to FIG. 1, the remote controller 96 is provided herein. A plurality of buttons 98a to 98g and an infrared transmitting device 100 are provided in the remote controller 96. As the buttons 98a to 98g are pressed, infrared signals corresponding to the respective buttons are transmitted.

The button 98a is a button for inputting an injection quantity per unit time. The button 98b is a button for inputting a temporary increase quantity of medicine. The button 98c is a set/release button used for setting up the inputted amounts or releasing the setup amounts. The button 98d is a start/stop button and performs the same function as the button 94a. The button 98e is a high-speed movement button that is used when a user intends to have the medicine arrive at the end of the tube by means of the piston 14 just before the medicine is injected into the patient, that is, when the user intends to rapidly push out the medicine. The button 98f is a retraction button for causing the moving member 42 to retract. The button 98g is a preliminary movement button for causing the moving member 42 to rapidly move toward the piston 14 until the member comes into contact with the piston, when the leading end portion of the moving member 42 is spaced apart from the rear portion of the piston 14.

Figure 5:
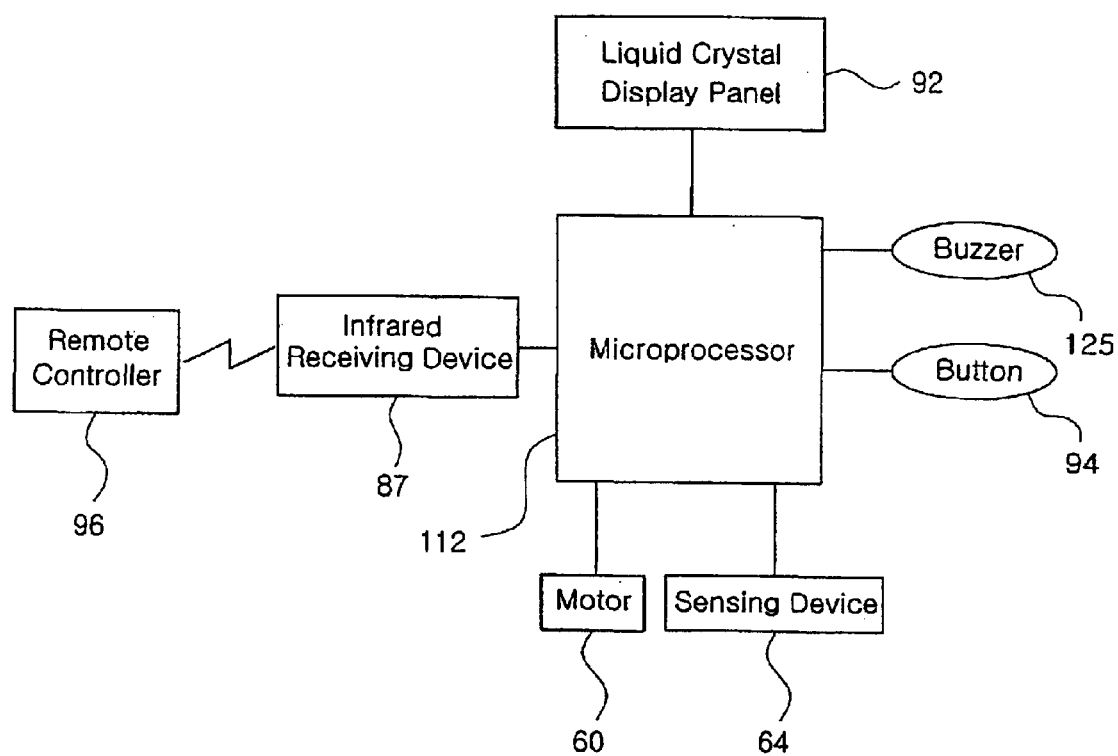
FIG. 5 is a structural view of a control device provided in the medicine injection apparatus shown in FIG. 1.

Referring to FIG. 5, the circuit board 84 is provided with a controlling microprocessor 112. A one-chip microcomputer with a memory incorporated therein is preferable to be used as the microprocessor. The microprocessor 112 is called a micom, and includes an operating and processing unit and a memory. Each circuit device is connected to the microprocessor 112. FIG. 5 shows the connection condition.

The infrared receiving device 87 is connected to the microprocessor 112. Therefore, the signals obtained by pressing the buttons 98a to 98g of the remote controller 96 are transmitted to and processed in the microprocessor 112. The front panel 90 including the liquid crystal display 92 and some buttons is also connected to the microprocessor 112, and information is outputted from the panel according to the instructions, or the contents inputted by the buttons are transferred to the microprocessor 112.

The motor 60 and the sensing device 64 are connected to the microprocessor 112. According to the control of the microprocessor, the power source is supplied to the motor 60, which in turn rotates. It is transferred from the sensing device 64 to the microprocessor 112 whether light is transferred to the light-receiving element, and the microprocessor 112 monitors an operating condition of the injection apparatus on the basis of the above result.

A buzzer 125 is connected to the microprocessor 112. The buzzer 125 is controlled to ring when malfunction occurs, i.e. when medicine is not injected, etc. or when all medicine is fully injected.

The microprocessor 112 processes data that is transferred from the circuit boards connected thereto and controls the operation of the motor, etc. to correspond to the injection quantity per unit time according to the button inputs. Such a control process will be easily understood by a person skilled in the art with reference to the following description.

Hereinafter, the operation of the medicine injection apparatus 10 is explained with reference to FIGS. 1, 3, 5 and 6A to 6D.

Figure 6A:
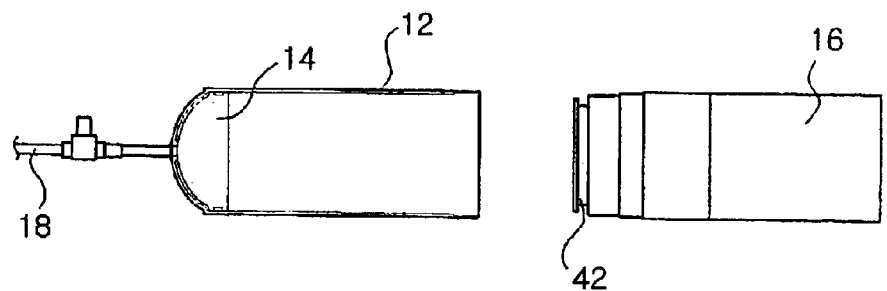
FIGS. 6A to 6D are views illustrating an operation of the medicine injection apparatus shown in FIG. 1.

As shown in FIG. 6A, the piston pushing apparatus 16 is coupled with the cylinder 12 at the rear portion thereof. The moving member 42 of the piston pushing apparatus 42 is retracted to the utmost. The injection quantity per unit time and instantaneous amount of change are set before the above coupling. If the button 98a for inputting the injection quantity per unit time is pressed, predetermined injection quantities per unit time (for example, 0.5 cc, 1.0 cc, 3.0 cc, 5.0 cc, 10.0 cc per unit time) are sequentially displayed in turn whenever the button is pressed. The injection quantity per unit time is set by pressing the set button 98c at a desired injection quantity per unit time. And then, the patient can press the button 94b when he feels a serious pain and intends to increase the quantity of medicine to be injected into him, and thereby the increased quantity can be set. That is, the increased injection quantity can be set in a manner that the user presses the set button 98c at the set point of the desired increased quantity among predetermined increased quantities (for example, 0.5 cc, 1.0 cc, 3.0 cc, 5.0 cc, 10.0 cc per unit time) that are sequentially displayed when the user presses the button 98b.

Figure 6B:
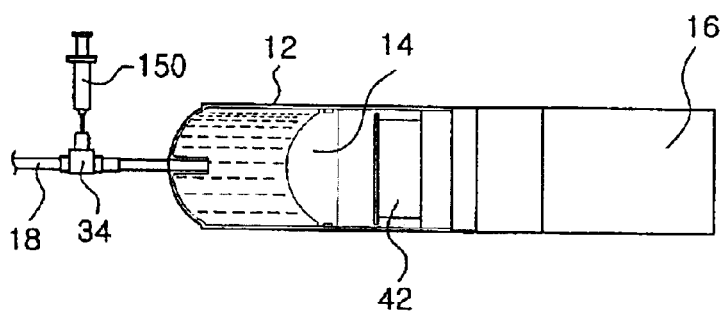

As shown in FIG. 6B, the medicine is injected into the cylinder 12 after the piston pushing apparatus 16 is coupled therewith. At this time, the medicine is transferred into the cylinder 12 by pushing the syringe plunger into a Luer lock portion of the syringe portion connected to T-shaped valve 34 (supply valve member) installed to inject the medicine into a syringe 150. And this time, the air remaining in the cylinder is discharged through a gap between the devices. On the contrary, the piston pushing apparatus 16 may be coupled with the cylinder after the medicine is beforehand injected therein.

Figure 6C:
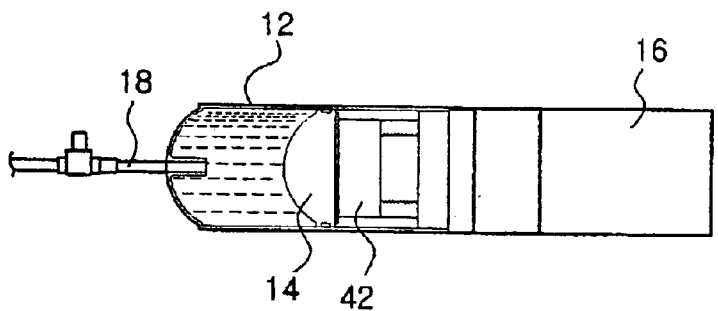
Figure 6D:
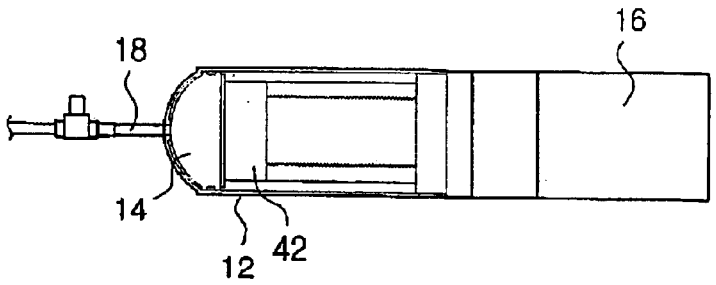

Thereafter, as shown in FIG. 6C, the user presses the preliminary movement button 98g to cause the moving member 42 to move in a longitudinal direction. The moving member 42 stops moving when it comes into contact with the piston 14. And then, the user connects an end of the tube 18 to the passage connected to the needle that is inserted into a vein of the patient, after he advances the medicine by pressing the high-speed movement button 98e. Upon pressing the start/stop buttons 98d and 94a, the injection starts. As shown in FIG. 6D, if the injection is completed, the user retracts the moving member 42 by pressing the retraction button 98f. Thereafter, the user separates the end of the tube 18 from the passage connected to the needle that is inserted into the patient's vein.

After use, the piston pushing apparatus 16 is separated from the cylinder 12, and the cylinder 12, the piston 14, the tube 18, etc. are discarded. The piston pushing apparatus may be reused.

On the other hand, when the doctor intends to temporarily increase the injection quantity of medicine during injection, the doctor presses the temporary increase button 94b. When it is necessary to stop injecting the medicine in the middle of injection, the injection is stopped by pressing the start/stop buttons 94a and 98d. The medicine cannot be injected if the needle is not correctly inserted into the patient's vein. If the medicine is injected in this case, the patient will feel pain. At this time, although electric power is supplied to the motor, the motor cannot rotate or cannot rotate at a speed proportional to the set injection quantity per unit time. Thus, the rotary encoder 66 stops or retards its rotation. Consequently, the number of pulses generated by a light that is transferred from the light-emitting element to the light-receiving element is zero or below the predetermined number. The microprocessor 112 continues to detect the number of pulses, and it causes the moving member 42 to automatically retract when the above condition is detected.

Figure 7A:
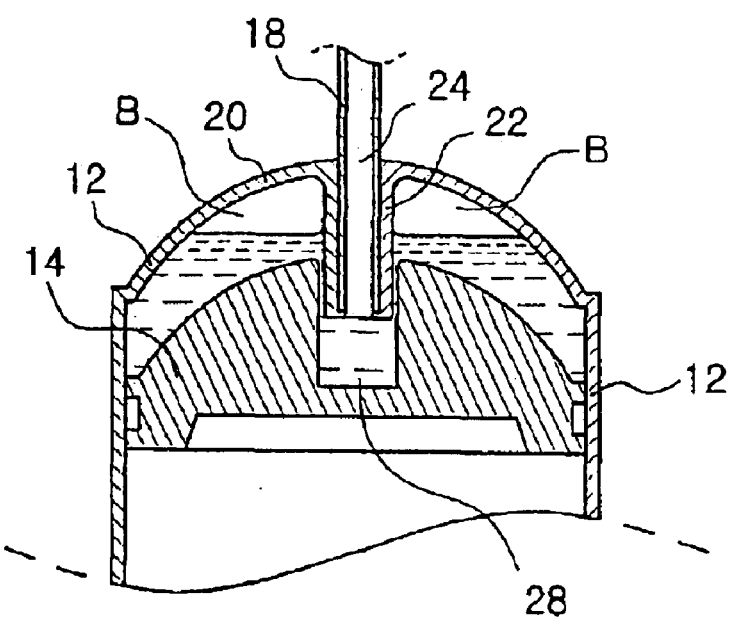
FIGS. 7A and 7B are partial sectional views illustrating a state wherein air injection is delayed in the medicine injection apparatus of FIG. 1.
Figure 7B:
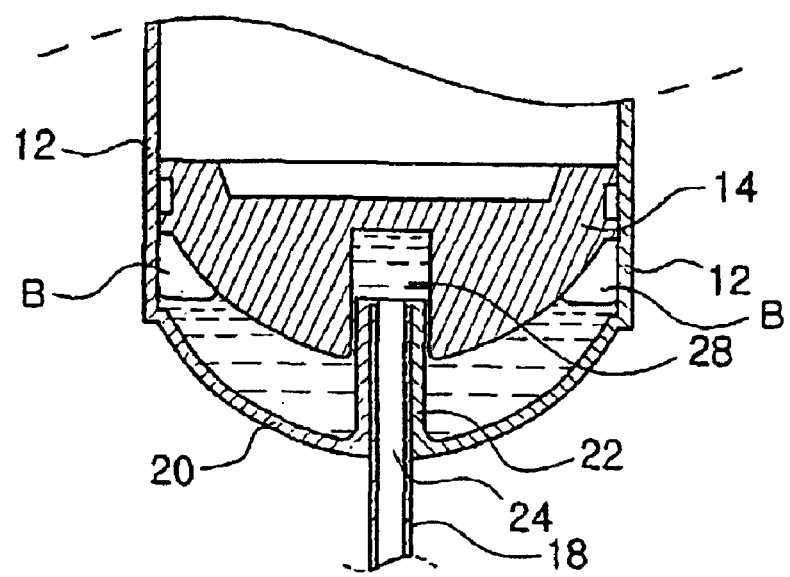

FIGS. 7A and 7B show the conditions wherein the medicine in the cylinder 12 is almost injected. When the medicine is supplied into the cylinder 12, the air remaining in the tube may be introduced into the cylinder. If possible, it is preferred that the air not be injected into the patient. As shown in FIGS. 7A and 7B, if a bubble is generated within the cylinder 12, the bubble is always located in an upper part.

FIG. 7A shows a condition wherein the head portion 20 of the cylinder 12 faces upward. Bubble B is formed at an innermost end of the head portion 20, and the end of the exhaust projection 22 is located lower than the bubble B. Therefore, the exhaust projection 22 continues to be located within the medicine. Consequently, the air can be discharged only after the medicine is injected.

FIG. 7B shows a condition wherein the head portion 20 of the cylinder 12 faces downward. The bubble B is formed at a peripheral portion of the piston 14. The bubble B is always located at the peripheral portion of the piston 14, although the piston 14 moves under this condition. Consequently, the air can be discharged only after the medicine is injected.

The medicine injection apparatus according to the embodiment of the aforementioned construction can inject the medicine while keeping the injection quantity of medicine per unit time constant. Further, the injection speed of medicine can be set directly by the doctor or under the supervision of the doctor, and it can be adjusted in the range of the doctor's settings. The stop of the medicine injection is easily accomplished. Additional injection can be stopped by the detection of the condition that the medicine may not be injected into the patient's vein according to the needle conditions. Furthermore, the likelihood of introduction of air into the patient during the medicine injection is reduced and the medicine leakage can also be reduced.

Figure 8A:
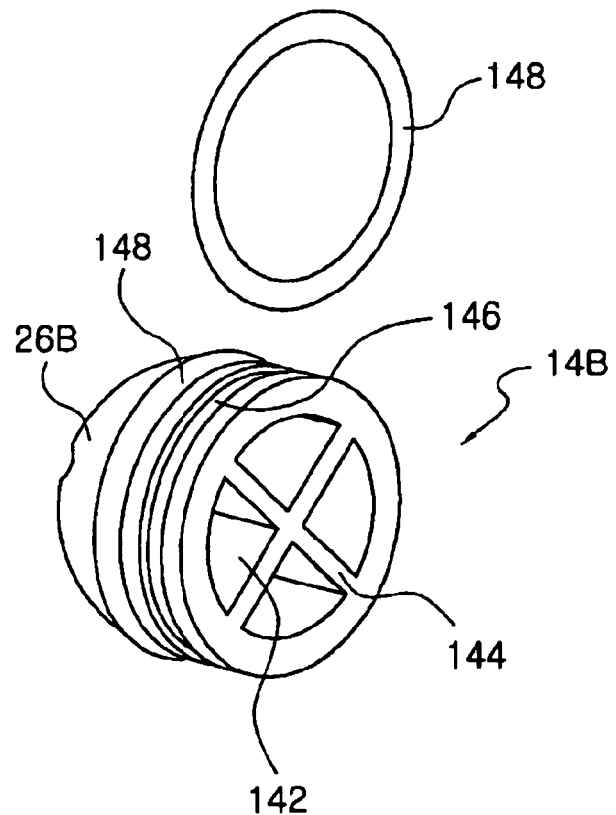
FIGS. 8A and 8B are an exploded perspective view and a sectional view, respectively, of a piston used in a medicine injection apparatus according to another embodiment of the present invention.
Figure 8B:
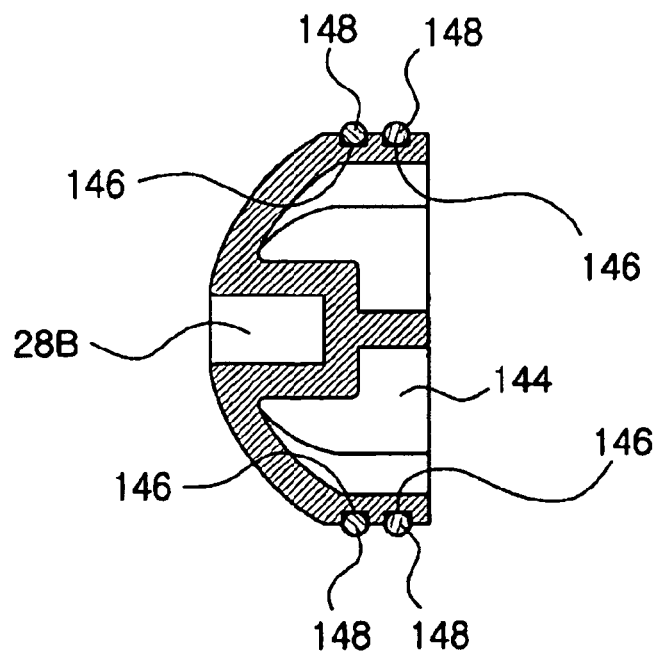

Referring to FIGS. 8A and 8B, there is shown a piston used for a liquid injection apparatus according to another embodiment of the present invention. The piston 14B is injection-molded from plastic resin. The piston has a generally short cylindrical body and a round leading end 26B. A distal portion of the leading end is provided with a recess 28B similar to the previous embodiment. A rear portion of the piston is provided with a flesh-removing recess 142 which is provided with ribs 144 therein.

An outer surface of the cylindrical body is provided with two ring-type (annular) grooves 146 side by side. Sealing rings (for example, O-rings) 148 are fitted into the grooves. Each groove 146 has a rectangular cross-section as shown in FIG. 8B, and each sealing ring 148 has a circular cross-section. When the piston is inserted into the cylinder with the sealing rings 148 fitted into the grooves, the sealing rings 148 are deformed and wedged into corners of the grooves 146. Thus, the piston can move smoothly while maintaining the liquid-tight sealing, and the sealing rings 148 are deformed outward to reduce possibility of breakaway of the sealing rings 148.

Figure 9:
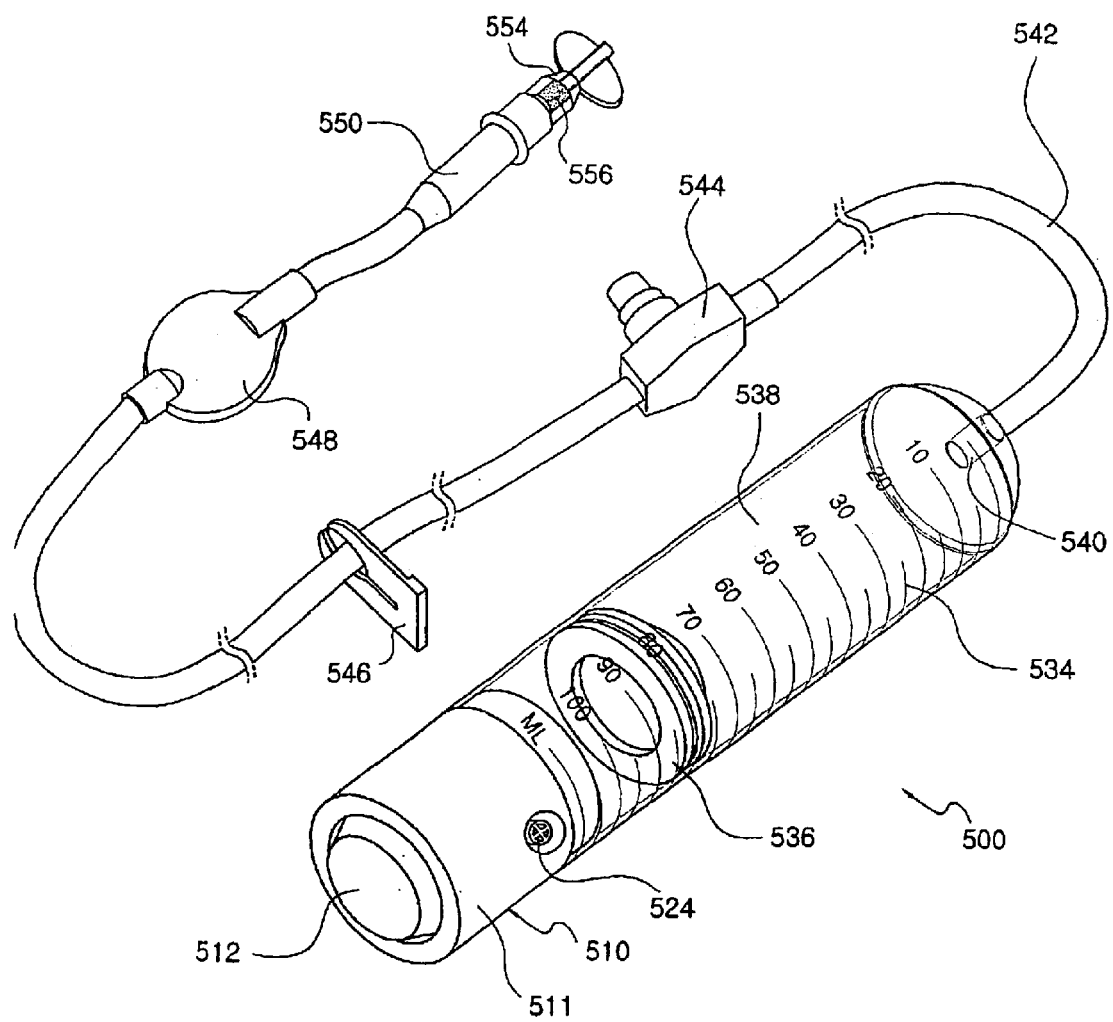
FIG. 9 is a perspective view of a medicine injection apparatus according to a further embodiment of the present invention.
Figure 10:
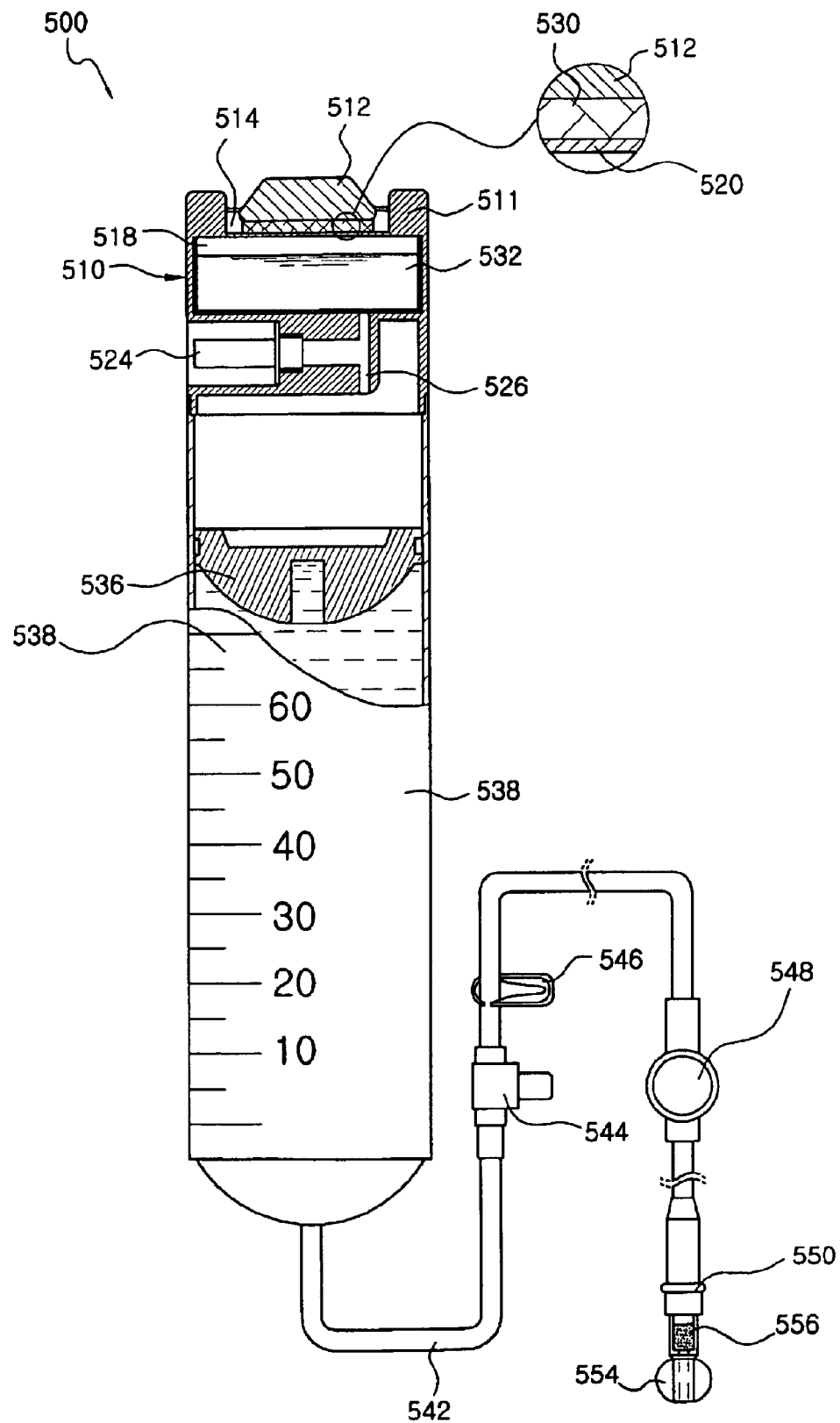
FIG. 10 is a front and partially cut-away view of the medicine injection apparatus of FIG. 9.
Figure 11:
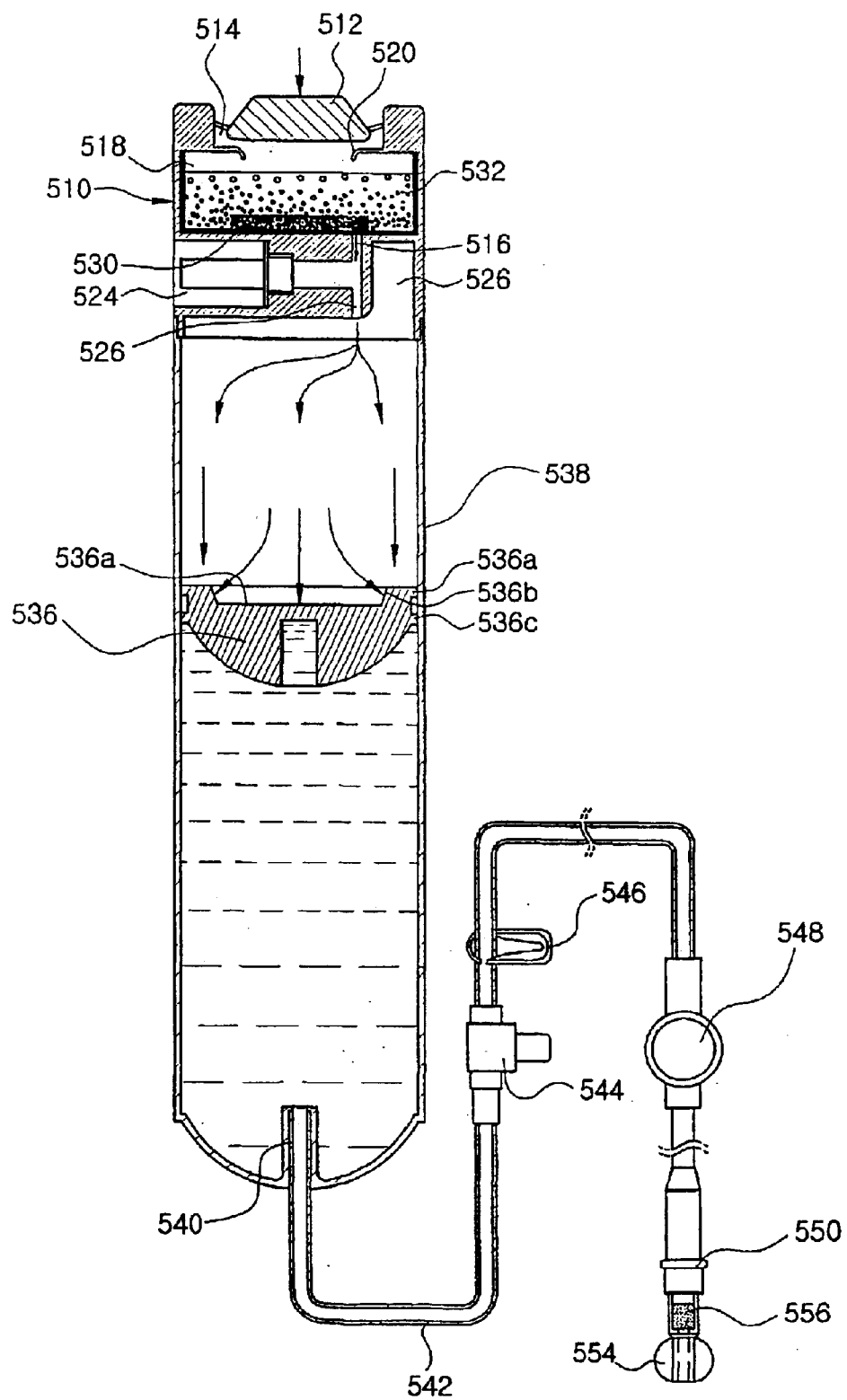
FIG. 11 is a transverse sectional view of the medicine injection apparatus for illustrating its condition of use.

FIGS. 9 to 11 show a liquid injection apparatus according to a further embodiment of the present invention. Referring to FIGS. 9 to 11, the liquid injection apparatus 500 has a cylinder 538, a piston 536, and a gas supply apparatus 510 serving as a piston pushing apparatus for applying pressure to the piston.

The gas supply apparatus 510 has an upper chamber 514 and a lower chamber 518 in a housing 511 thereof. The upper and lower chambers 514 and 518 are separated by a partition 520. The partition 520 can be torn by a predetermined pressure. The bottom of the lower chamber 518 is provided with a gas passage 526.

The central portion of an upper surface over the upper chamber 514 of the gas supply apparatus 510 is provided with a pressing plate 512 in the form of disk. A user can press the pressing plate 512. The pressing plate 512 is connected to other portions of the housing with a deformable thin wall interposed between them.

The upper chamber 514 contains a disk-type solid material 530 therein on the partition 520. The solid material 530 mainly consists of a material which can react with liquid and produce gas. In an embodiment of the present invention, the solid material containing sodium bicarbonate ($NaHCO_3$) as a main component can be used together with gelatin. Preferably, the solid material consists of 70–95 wt % of sodium bicarbonate ($NaHCO_3$), 3–30 wt % of gelatin, and no more than 3 wt % of Talc. Most preferably, the solid material consists of 90–94 wt % of sodium bicarbonate ($NaHCO_3$), 5–10 wt % of gelatin, and no more than 1 wt % of Talc. In the process of generation of gas, it is necessary to maintain gas having a constant pressure during a required period of time. By adjusting the amount of gelatin, the pressure and the period of time can be controlled. It is preferred to use Talc for making the material into solid.

The lower chamber 518 below the partition 520 is provided with a gas-permeable flexible sheet 528 over the periphery and the bottom of the lower chamber. The sheet functions as a gas-permeable but liquid-impermeable filter. Referring to FIG. 12(a), the sheet 528 is formed by sequentially laminating three layers, that is, a liquid-impermeable but gas-permeable membrane 528a, a nonwoven fabric sheet 528b, preferably made of synthetic fiber, capable of passing or retaining gas to form a gas passage, and a liquid- and gas-impermeable flexible film 528c. The film 528c is located on the side of the housing 511. As for the film 528c, it is preferable to use a normal soft transparent vinyl sheet. Instead of the nonwoven fabric sheet, it is also possible to use a pliable and porous foam body such as sponge.

FIG. 12(b) is a development view of the sheet 528 which is provided with an outermost bonding line 528d and a coupling line 528e for coupling the three layers. At the bonding line 528d, a circular plate and a side plate are bonded together. The three layers are coupled together at the bonding line 528d and the coupling line 528e and preferably fusion-bonded by applying heat and pressure thereto.

As understood from FIG. 12(a), the film 528c is formed with an aperture 528f at the position where the aperture communicates with the gas passage 526. In order to prevent the liquid in the lower chamber 518 from accessing the position of the aperture 528f, the film 528c is attached to the inner wall of the lower chamber 518. Preferably, in the vicinity of the corners of the lower chamber 518, the film is attached to the wall of the lower chamber over all the periphery of the lower chamber. The aperture 528c communicates with the gas passage 526.

Figure 12:
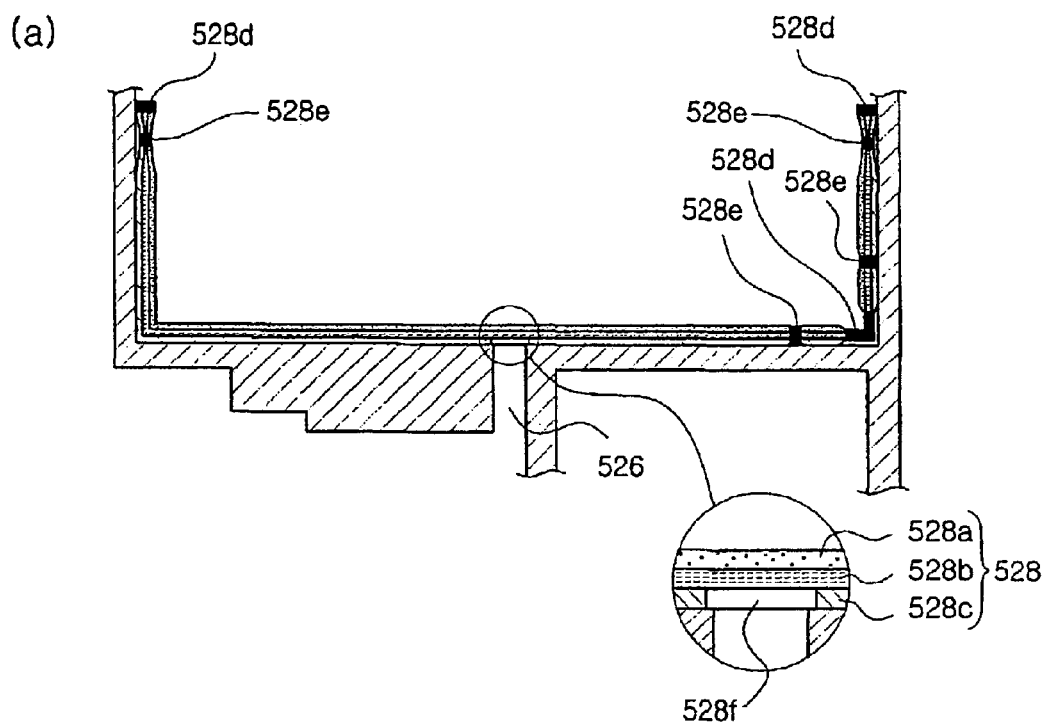
FIG. 12(a) is a partial sectional view of a gas supply apparatus with plural sheets of a gas-permeable material installed therein.
FIG. 12(b) is a development view of the gas-permeable sheet of FIG. 12(a).
Figure 12:
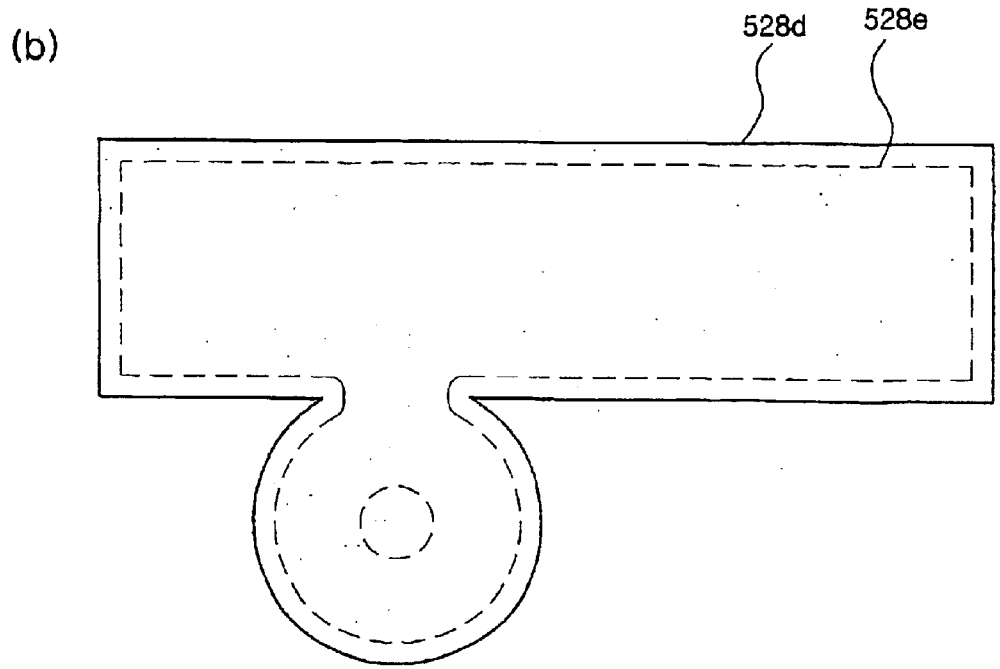

Referring to FIGS. 11 and 12, although a major portion of the surface of the membrane is in contact with the liquid material, at least some portions thereof are not in contact with the liquid material. Generated second gas enters the layer of nonwoven fabric sheet through the membrane at the portion where it is not in contact with the liquid material. Since the layer of nonwoven fabric sheet forms a gas-moving path, the gas can move via the path to the aperture 528f through which the gas can be then discharged.

The liquid material 532 is accommodated in the lower chamber 518 that is surrounded by the sheet 528. The liquid material 532 consists of a L-tartaric acid ($C_4H_6O_6$) solution. An L-tartaric acid ($C_4H_6O_6$) aqueous solution in a liquid phase does not leak downward due to liquid sealing effect of the sheet 528.

The gas passage 526 is formed below the lower chamber 518. The gas passage 526 is connected to the portion of the cylinder 538 behind the piston 536. A side portion of the housing 511 is provided with an aperture connected to the gas passage 526, and the aperture is provided with a pressure-regulating valve 524. The pressure-regulating valve 524 adjusts pressure, for example, by discharging (purging) the gas outward when the pressure exceeds a reference pressure (See FIG. 12.). The pressure-regulating valve may be of a conventional type.

The cylinder 538 is connected to the lower portion of the gas supply apparatus 510. In the embodiment shown in FIGS. 9 to 12, the cylinder 538 and the piston 536 are identical to those of the embodiment shown in FIG. 1. Like the previous embodiment, a circular recess 536a is formed in the rear portion of the piston 536.

On the other hand, a tube 542 is inserted and fixed into an outlet 540 of the cylinder 538. A supply valve (T-shaped valve) 544 for supplying the cylinder 538 with an injection medicine is installed at a predetermined position in the tube 542. A clamp 546 is also provided for blocking a stream of the injection medicine from flowing along the tube 542 when desired. A filter 548 is fitted into the tube for filtering a foreign substance such as air contained in the injection medicine. An injection quantity adjustor 550 is installed at a distal end of the tube 542. The injection quantity adjustor 550 finally adjusts the injection quantity of medicine per unit time. The adjustor 550 can be connected via a connector, not shown, to a needle or an extension tube of a catheter stuck into the skin of a patient. Before use thereof, a cap 554 is fitted into the adjustor 550 as shown in FIGS. 9 to 11. The cap is illustrated as a transparent cap in the figures. The interior of the cap 554 is formed with a through-hole. A closure 556 is fitted into the through-hole and is liquid-impermeable but gas-permeable. The material for the closure is available from Porex Corporation (web site: www.porex.com) located in Fairburn, Ga. 30213, U.S.A.

Hereinafter, the operation of the liquid injection apparatus constructed as such will be described with reference to FIGS. 10 and 11.

First, the cylinder 538 is coupled with the gas supply apparatus 510. After the gas supply apparatus 510 is coupled with the interior of the cylinder 538, the connection portion of them is sealed with a tape or the like. (Otherwise, the gas supply apparatus 510 may be originally manufactured integrally with the cylinder.)

The injection medicine is first injected into the cylinder 538 through the injection medicine supply valve 544 attached to the tube 542. At this time, the injection medicine pushes the piston 536 in the cylinder 538 upward and fills the cylinder 538.

At this time, since the piston 536 is pushed upward and the air in the space above the piston 536 leaks out through the pressure-regulating valve 524, the cylinder 538 is easily filled with the injection medicine.

As mentioned above, with the cylinder 538 filled with the injection medicine, a user presses the pressing plate 512 in the upper chamber 512 of the gas supply apparatus 510 with predetermined force. Then, the pressing plate 512 is pushed downward and presses the solid material 530 on the inner side with respect to the pressing plate. Next, the solid material 530 tears the partition 520, and is expelled therefrom, and then is dipped into the liquid material 532 within the lower chamber 518. Simultaneously, the solid and liquid materials 530 and 532 react and generate gas.

When the solid material 530 containing sodium bicarbonate ($NaHCO_3$) as a main component comes into a contact with the L-tartaric acid ($C_4H_6O_6$) solution, they chemically react and generate carbon dioxide ($CO_2$) gas.

The chemical reaction between the solid and liquid materials 530 and 532 is expressed as the following equation:

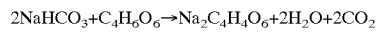

$$2NaHCO_3 + C_4H_6O_6 \rightarrow Na_2C_4H_4O_6 + 2H_2O + 2CO_2$$

As aforementioned, the generated carbon dioxide gas leaks out through the sheet 528 surrounded by the lower chamber 518 and then passes through the gas passage 526. The pressure of the generated carbon dioxide gas is generally determined at a certain degree in the mixing process of raw materials upon manufacturing the solid material. The pressure-regulating valve 524 can adjust the discharge pressure of the carbon dioxide gas passing through the gas passage 526, for example, to maintain the pressure at 0.35 $kg/cm^2$ to 0.50 $kg/cm^2$. That is, if the carbon dioxide gas flows into the pressure-regulating valve at high pressure of the maximum 0.50 kg/cm or more, the carbon dioxide gas of 0.50 $kg/cm^2$ is supplied via a second gas outlet 522. The remainder of the gas exceeding the maximum pressure is discharged outward through the pressure-regulating valve 524. In other embodiments, the discharge pressure of the carbon dioxide gas may be set within a range different from the above range.

The carbon dioxide gas flows into the cylinder 538 via the gas passage 526 while maintaining constant pressure. The carbon dioxide gas which flows into the cylinder pushes the piston 536 in the cylinder 538 downward. The piston 536 moves downward at a constant speed by constant gas pressure.

The piston 536 is pushed and the injection medicine in the cylinder 538 is discharged through the outlet 540 formed at the lower end of the cylinder 538. In response to the constant amount of movement of the piston 536, the injection medicine is discharged into the tube 542 while maintaining a constant injection quantity per unit time.

On the other hand, if it is necessary to temporarily block the injection medicine flowing along the tube 542, the clamp 546 is moved toward one side thereof to tighten the tube 542, thereby temporarily blocking the stream of the injection medicine. A patient can easily observe the supply conditions of the injection medicine by means of the scale 534 on the surface of the cylinder 538 for indicating the remaining and discharging quantity of the injection medicine during injection of the medicine. Finally, the injection quantity per unit time can be controlled by the adjustor 550 at the distal end of the tube.

On the other hand, when the piston is moved in the cylinder, the pressure of gas is applied normally onto the whole surface of the rear portion of the piston 536. The pressure of gas is also applied onto a side wall 536b of the circular recess 536a in the rear portion of the piston 536. The pressure of gas pushes the side wall 536b and allows peripheral projections 536c to be pushed toward the inner wall of the cylinder, thereby firmly reducing the leakage of the injection medicine.

The cylinder, the piston and the gas supply apparatus are discarded after they are used. The liquid injection apparatus of the embodiments can inject the injection medicine at a constant speed for a long time only by simple operation.

Although the present invention has been illustrated and described with reference to the exemplified embodiments of the present invention, it should be understood that various changes, modifications and additions to the present invention can be made without departing from the spirit and scope of the present invention.

What is claimed is:

1. A liquid supply apparatus, comprising:
   a cylinder having an interior space, a head portion and a rear portion, the head portion having a liquid-flow opening;
   a piston located in the interior space of the cylinder and air-tightly partitioning the interior space into a liquid compartment on the side of head portion and a gas compartment on the side of the rear portion;
   a gas supply apparatus configured to be coupled to the rear portion and to supply a gas into the gas compartment, the gas supply apparatus comprising:
      a liquid material configured to be used to generate the gas, and
      a gas separating structure configured to separate the generated gas from the liquid, the gas separating structure comprising a liquid-impermeable-but-gas-permeable sheet in contact with the liquid material; and
   wherein the piston is configured to move toward the head portion when the gas is supplied to the gas compartment.

2. The liquid supply apparatus of claim 1, wherein the gas supply apparatus further comprises a solid material capable of generating the gas by a chemical reaction with the liquid material.

3. The liquid supply apparatus of claims 2, wherein the solid material contains a metal carbonate.

4. The liquid supply apparatus of claim 2, wherein the solid material comprises 70–95 wt % of sodium bicarbonate ($NaHCO_3$), 3–30 wt % of gelatin, and no more than 3 wt % of talc.

5. The liquid supply apparatus of claim 2, wherein the solid material comprises 90–94 wt % of sodium bicarbonate ($NaHCO_3$), 5–10 wt % of gelatin, and no more than 1 wt % of talc.

6. The liquid supply apparatus of claims 2, wherein the liquid material is a solution of L-tartaric acid ($C_4H_6O_6$).

7. The liquid supply apparatus of claim 1, wherein the gas supply apparatus is configured to generate the gas at a pressure from about 0.35 $kg/cm^2$ to about 0.50 $kg/cm^2$.

8. The liquid supply apparatus of claim 1, wherein the gas supply apparatus further comprises:
a second material;
a breakable partition isolating the liquid material and the second materials from each other;
a reaction vessel where the liquid and second materials react with each other when the partition is broken; and
a partition breaker configured to break the breakable partition so as to let the liquid and second material contact each other in the reaction vessel.

9. The liquid supply apparatus of claim 8, wherein the reaction vessel is a container containing the liquid material.

10. A liquid supply apparatus comprising:
a cylinder having an interior space, a head portion and a rear portion, the head portion having a liquid-flow opening;
a piston located in the interior space of the cylinder and air-tightly partitioning the interior space into a liquid compartment on the side of head portion and a gas compartment on the side of the rear portion;
a gas supply apparatus configured to be coupled to the rear portion and to supply a gas into the gas compartment;
wherein the piston is configured to move toward the head portion when the gas is supplied to the gas compartment; and
wherein the gas supply apparatus comprises:
a first material,
a second material,
a breakable partition isolating the first and second materials from each other,
a reaction vessel where the first and second materials react with each other when the partition is broken,
a partition breaker configured to break the breakable partition so as to let the first and second material contact each other in the reaction vessel, and
a gas collecting structure comprising a liquid-impermeable-but-gas-permeable sheet arranged to contact the liquid.

11. The liquid supply apparatus of claim 10, wherein the liquid-impermeable-but-gas-permeable sheet is placed on a wall of the reaction vessel such that at least a portion of the sheet is exposed to the gas generated from the reaction.

12. The liquid supply apparatus of claim 10, wherein the gas collecting structure further comprises a gas-passage sheet and a liquid-and-gas-impermeable sheet, and wherein the gas-passage sheet is located between the liquid-impermeable-but-gas-permeable sheet and the liquid-and-gas-impermeable sheet.

13. The liquid supply apparatus of claim 12, wherein the gas-passage sheet is made of non-woven fabric or foam material.

14. A liquid supply apparatus, comprising:
a cylinder having an interior space, a head portion and a rear portion, the head portion having a liquid-flow opening;
a piston located in the interior space of the cylinder and air-tightly partitioning the interior space into a liquid compartment on the side of head portion and a gas compartment on the side of the rear portion;
a gas supply apparatus configured to be coupled to the rear portion and to supply a gas into the gas compartment;
wherein the piston is configured to move toward the head portion when the eas is supplied to the gas compartment; and wherein the gas supply apparatus comprises:
a first material,
a second material,
a breakable partition isolating the first and second materials from each other,
a reaction vessel where the first and second materials react with each other when the partition is broken,
a partition breaker configured to break the breakable partition so as to let the first and second material contact each other in the reaction vessel, and
a gas pressure regulator configured to control or regulate the pressure of the gas supplied into the gas compartment.

15. The liquid supply apparatus of claim 1, wherein the head portion of the cylinder comprises a projection extending into the interior space and has a longitudinal through-hole, the through-hole constituting the liquid-flow opening.

16. The liquid supply apparatus of claim 15, wherein the piston has a leading end facing the projection, wherein the piston has a recess on the leading end thereof, and wherein the recess is configured to receive the projection.

17. The liquid supply apparatus of claim 15, wherein the recess is further configured to substantially contact with the projection when receiving the projection.

18. The liquid supply apparatus of claim 15, further comprising a tube connected to the cylinder via the through-hole of the projection, wherein the tube is in fluid communication with the liquid compartment.

19. A liquid supply apparatus, comprising:
a cylinder having an interior space, a head portion and a rear portion, the head portion having a liquid-flow opening;
a piston located in the interior space of the cylinder and air-tightly partitioning the interior space into a liquid compartment on the side of head portion and a gas compartment on the side of the rear portion;
a gas supply apparatus configured to be coupled to the rear portion and to supply a gas into the gas compartment;
a tube connected to the liquid-flow opening and in fluid communication with the liquid compartment;
a cap configured to cover a distal end of the tube, the cap having a through-hole in fluid communication with the tube, the cap further comprising a gas-permeable-but-liquid-impermeable material located between the through hole and the distal end of the placed and configured to allow passage of a gas from the tube through the through-hole while preventing passage of a liquid through the through-hole;
wherein the piston is configured to move toward the head portion when the gas is supplied to the gas compartment.

20. The liquid supply apparatus of claim 1, wherein the piston has a recess on a trailing end thereof.

21. A method of continuously supplying a liquid for an extended period of time, the method comprising:
providing the liquid supply apparatus of claim 1;
filling the liquid compartment with a liquid;
activating the gas supply apparatus so as to supply the gas into the gas compartment, wherein the gas supply apparatus continuously supplies the gas into the gas compartment for an extended period of time; and
wherein the piston is moved toward the head portion as a gaseous pressure within the gas compartment increases, whereby the liquid in the liquid compartment flows out of the liquid compartment through the liquid-flow opening.

22. The method of claim 21, wherein the liquid is a liquid medication.

23. The liquid supply apparatus of claim 19 wherein the head portion of the cylinder has a projection extending into the interior space and a longitudinal through-hole in the projection; and wherein the piston has a leading end facing the projection and a recess on the leading end thereof, the recess being configured to receive the projection.

24. The liquid supply apparatus of claim 23, wherein the recess is further configured to substantially contact with the projection when receiving the projection.

25. The liquid supply apparatus of claim 23, further comprising a tube connected to the cylinder via the through-hole of the projection, wherein the tube is in fluid communication with the liquid compartment.

26. The liquid supply apparatus of claim 23, wherein the piston has a recess on a trailing end thereof.

27. The liquid supply apparatus of claim 23, wherein the piston comprises a cylindrical body and a sealing ring, wherein the cylindrical body has an annular groove on an outer surface thereof, and wherein the sealing ring is fitted around the groove.

28. A cap for covering a liquid supply tube, comprising:

a cap body configured to cover an end of a liquid supply tube;

a through-hole formed on the cap body, the through-hole being in fluid communication with the liquid supply tube; and a gas-permeable-but-liquid-impermeable material configured to allow passage of a gas from the tube through the through-hole while preventing passage of a liquid through the through-hole.

29. The cap of claim 28, wherein the cap body is configured to tightly receive the end of the liquid supply tube.

* * * * *